US011272739B2

(12) United States Patent
Schmidt et al.

(10) Patent No.: US 11,272,739 B2
(45) Date of Patent: Mar. 15, 2022

(54) VAPORISER UNIT FOR AN INHALER, AND METHOD FOR CONTROLLING A VAPORISER UNIT

(71) Applicant: HAUNI MASCHINENBAU GMBH, Hamburg (DE)

(72) Inventors: Rene Schmidt, Buchholz i.d.N. (DE); Marc Kessler, Hamburg (DE); Sven Bohne, Hamburg (DE); Hoc Khiem Trieu, Westergellersen (DE); Karen Kalaydzhyan, Hamburg (DE)

(73) Assignee: HAUNI MASCHINENBAU GMBH, Hamburg (DE)

( * ) Notice: Subject to any disclaimer, the term of this patent is extended or adjusted under 35 U.S.C. 154(b) by 383 days.

(21) Appl. No.: 16/342,044

(22) PCT Filed: Oct. 26, 2017

(86) PCT No.: PCT/EP2017/077459
§ 371 (c)(1),
(2) Date: Apr. 15, 2019

(87) PCT Pub. No.: WO2018/083007
PCT Pub. Date: May 11, 2018

(65) Prior Publication Data
US 2019/0246696 A1 Aug. 15, 2019

(30) Foreign Application Priority Data

Nov. 1, 2016 (DE) .......................... 102016120803.5

(51) Int. Cl.
*A24F 47/00* (2020.01)
*A24F 40/46* (2020.01)
(Continued)

(52) U.S. Cl.
CPC ............ *A24F 40/46* (2020.01); *A24F 40/485* (2020.01); *A24F 40/50* (2020.01); *A61M 11/042* (2014.02);
(Continued)

(58) Field of Classification Search
CPC ......... A24F 40/46; A24F 40/50; A24F 47/008
See application file for complete search history.

(56) References Cited

U.S. PATENT DOCUMENTS 10,149,498 B2 * 12/2018 Batista ..................... A24F 40/70
10,612,770 B2 * 4/2020 Meinhart .............. B05B 7/1686
(Continued)

FOREIGN PATENT DOCUMENTS

AT 509046 B1 6/2011
CN 204048047 U 12/2014
(Continued)

OTHER PUBLICATIONS

First Examination Report issued by the Japanese Patent Office dated Aug. 26, 2020 for parallel Japanese Patent Application No. 2019-522986.
(Continued)

*Primary Examiner* — Neil Abrams
(74) *Attorney, Agent, or Firm* — Saliwanchik, Lloyd & Eisenschenk (57) ABSTRACT

The invention relates to a vaporiser unit for an inhaler, comprising a vaporiser body which consists of an electrically conductive substrate with an inlet side, an outlet side, and a plurality of micro-channels each of which extend through said substrate from the inlet side to the outlet side, and a resistive heating element for vaporising liquid conveyed through said micro-channels. The resistive heating element is formed by the substrate.

23 Claims, 3 Drawing Sheets

(51) Int. Cl.
*A61M 15/06* (2006.01)
*A24F 40/485* (2020.01)
*A24F 40/50* (2020.01)
*A61M 11/04* (2006.01)
*H05B 3/42* (2006.01)
*A24F 40/10* (2020.01)

(52) U.S. Cl.
CPC .............. *A61M 15/06* (2013.01); *H05B 3/42* (2013.01); *A24F 40/10* (2020.01); *A61M 2205/3653* (2013.01); *A61M 2205/8206* (2013.01)

(56) References Cited

U.S. PATENT DOCUMENTS

| | | | |
|---|---|---|---|
| 10,617,154 B2 * | 4/2020 | Phan | A24F 40/46 |
| 2013/0081623 A1 | 4/2013 | Buchberger | |
| 2014/0238424 A1 * | 8/2014 | Macko | A24F 40/46 |
| | | | 131/328 |
| 2014/0251324 A1 † | 9/2014 | Xiang | |
| 2015/0059780 A1 | 3/2015 | Davis et al. | |
| 2016/0007653 A1 | 1/2016 | Tu | |
| 2016/0021930 A1 | 1/2016 | Minskoff et al. | |
| 2016/0135505 A1 | 5/2016 | Li et al. | |
| 2016/0262454 A1 | 9/2016 | Sears et al. | |
| 2018/0249763 A1 * | 9/2018 | Schmidt | F04B 23/04 |
| 2020/0008473 A1 * | 1/2020 | Schmidt | A61M 15/06 |
| 2021/0186097 A1 * | 6/2021 | Schmidt | A24F 40/485 |
| 2021/0195952 A1 * | 7/2021 | Trieu | A61M 15/06 |

FOREIGN PATENT DOCUMENTS

| | | |
|---|---|---|
| CN | 204317492 U | 5/2015 |
| CN | 105208882 A | 12/2015 |
| CN | 105636467 A | 6/2016 |
| DE | 102014114133 A1 | 3/2016 |
| EP | 2399636 A1 | 12/2011 |
| EP | 3078281 A1 | 10/2016 |
| JP | 2010-208062 A | 9/2010 |
| WO | 2015/117701 A1 † | 8/2015 |
| WO | WO 2015 117701 A1 | 8/2015 |
| WO | 2016/064684 A1 † | 4/2016 |
| WO | WO 2016 064684 A1 | 4/2016 |
| WO | WO 2016/145072 A1 | 9/2016 |

OTHER PUBLICATIONS

Examination Report issued by the Chinese Patent Office dated Jan. 28, 2021 for parallel Chinese Patent Application No. 201780067945.7.

Examiner Report issued by the German Patent and Trademark Office in the priority application No. 10 2016 120 803.5, filed Nov. 1, 2016.

Third Party Submission under 37 CFR 1.290, attached concise description of relevance, and cited publications dated Jan. 7, 2020.

* cited by examiner
† cited by third party

VAPORISER UNIT FOR AN INHALER, AND METHOD FOR CONTROLLING A VAPORISER UNIT

CROSS REFERENCE TO RELATED APPLICATIONS

This application is a National Stage Application of International Application Number PCT/EP2017/077459, filed Oct. 26, 2017; which claims priority to German Patent Application No. 102016120803.5, filed Nov. 1, 2016.

The present invention relates to a vaporiser unit for an inhaler, comprising a vaporising member that comprises an inlet side, an outlet side, a plurality of microchannels, a substrate, and a resistance heating element for vaporising fluid conveyed through the microchannels.

Current electronic cigarettes that are based on the wick and coil principle, as are described by way of example in US 2016/0021930 A1, have various disadvantages. Firstly, the liquid vaporisation and metering are not separated from one another. Secondly, the amount of vapour and the heater temperature are directly related to one another, i.e. large amounts of vapour are associated with high heat outputs or vaporiser temperatures. Thirdly, inconsistent temperature ranges result at/in the region of the vaporiser, which is associated with the risk of local liquid overheating and harmful substances forming. Fourthly, the temperature prevailing in the vaporiser region at the wick-coil surface differs from the core temperature in the wick, as a result of which concentration changes in the liquid components occur during each individual vaporisation process and/or puff or draw. Said concentration change furthermore results in a gradual change in the composition of the liquid still located in the fluid reservoir, i.e. the amount of active substance released is not consistent either and changes from draw to draw.

The vaporiser unit known from US 2016/0262454 A1 comprises a vaporising member that is formed of the substrate, of capillary microchannels that are formed in the substrate in part and that are covered by a lid comprising microperforations in further part, as well as the fluid reservoir that is provided in the substrate and a vaporiser chamber which is provided in the substrate and in which the MEMS-based heater, which extends in a flat, planar manner, is arranged. The capillary microchannels that are constructed using thin-film layer technology and extend between the fluid reservoir and the vaporiser chamber are provided with valves as transport elements and are arranged in parallel with the thin-film layers or with the longitudinal extension of the substrate. During use, liquid is conveyed, by the action of capillary force, from the fluid reservoir, through the capillary microchannels, and to the inlet side of the vaporiser chamber, vaporised in the vaporiser chamber of the MEMS-based heater, and emitted on the outlet side of the vaporiser chamber through the lid comprising the microperforations. The MEMS-based heater, which extends in a flat and planar manner, can vaporise the liquid only to a limited extent, with the result that the vaporising performance achievable thereby is relatively low. The design having the fluid reservoir and the vaporiser chamber in the substrate is complex and requires a relatively large amount of installation space. Using the lid to cover the capillary microchannels that are formed in the substrate in part is associated with sealing problems, also between the capillary microchannels, as well as an increased manufacturing outlay.

The vaporiser unit known from US 2016/0007653 A1 is assembled from a circuit board comprising a printed circuit, a vaporising member that is arranged on the circuit board and is designed as a MEMS vaporiser chip, and a housing part in which the circuit board that carries the MEMS vaporiser chip is inserted having one end on a housing edge and so as to leave a storage chamber for liquid. The MEMS vaporiser chip is constructed in a multilayered manner according to thin-film layer technology, proceeding from a silicon substrate, and comprises a capillary microchannel assembly that is covered by a membrane, a resistance heater, and a resistance temperature sensor which are arranged on the side of the membrane remote from the microchannel assembly and extend over a portion of the microchannel assembly. The microchannels of the microchannel assembly are arranged such that the longitudinal axis thereof is in parallel with the thin-film layers and are formed in the silicon substrate in part and by a lid, in the form of the membrane, in further part. A cavity is formed at each of the two ends of the microchannel assembly, one of which cavities functions as a vaporisation outlet chamber and the other of which cavities functions, in cooperation with the inner walls of the housing part, as a storage chamber or as a fluid reservoir for liquid. During use, the liquid is continuously conveyed, by the action of capillary force, into the microchannel assembly and is vaporised by means of the resistance heater, as a result of which the liquid conveyance and the liquid vaporisation cannot be influenced separately from one another but are instead mutually dependent, which impedes more precise control or regulation of the vaporisation of liquid. The extensive resistance heater, which is spaced apart from the inside of the channel and from the liquid and is arranged on the outside of the membrane, can vaporise the liquid only to a limited extent, with the result that the vaporising performance achievable thereby is relatively low. The structure is thermally inert and is complex owing to a plurality of layers. Using the membrane to cover the microchannels that are formed in the substrate in part, are initially open at the top, and are produced in the form of grooves, is associated with sealing problems, also between the microchannels, as well as an increased manufacturing outlay.

The object of the invention is that of improving a known vaporiser unit in various respects, in particular increasing the vaporiser performance, reducing the complexity of the design, and allowing for a smaller installation space and/or reducing the sealing problem, as well as providing a simple, reliably and reproducibly functioning vaporiser unit for an inhaler which overcomes the above disadvantages and is capable of providing an amount of vapour having desired properties, such as the amount and composition, and specifying a corresponding control method.

This object is achieved by the invention by means of the features of the independent claims.

According to the invention, the resistance heating element is formed by the substrate such that the heater current flows directly through the substrate itself. In contrast with the prior art, the heater voltage is applied to the substrate itself. The heated substrate can directly vaporise the fluid contained in the microchannels. This direct transfer of heat to the fluid is significantly more effective and quicker than the known heating by means of a separate metal heater element.

The microchannels are preferably each surrounded by the substrate in the peripheral direction. In this way, effective vaporisation can be ensured in a compact design. The microchannels can be provided as it were with optimally actuatable full lateral surface heating in a simple manner, and covers which cause sealing problems, as are used in known vaporisation members, can be avoided.

A flow controller that controls the flow of fluid through the microchannels is preferably provided on the inlet side of the substrate. This allows the fluid that is to be vaporised to be metered precisely into the microchannels of the vaporiser. Furthermore, it is possible to ensure an aerosol quality, in particular vapour composition and droplet spectrum, that is constant for each draw, and a feedback effect on the fluid reservoir owing to inconsistent component vaporisation can be largely prevented. The microchannels can be filled with an exactly measured portion of fluid. The portion can be kept in the microchannels such that backflow is prevented, and can be provided for precisely portioned complete vaporisation. The flow controller may be designed for example in the form of one or more pumps and/or one or more valves.

In an advantageous embodiment, the flow controller is a flow-control layer comprising through-holes that extend through the flow-control layer. In this case, it is particularly advantageous for the contact angle between the fluid and the inner wall of one or each through-hole to be able to be varied by means of applying an electrical voltage that can be generated by a voltage source, or an electric field generated by the electrical voltage. As a result, the flow through the through-holes can advantageously be varied, in particular stopped, and/or released, in particular by reducing or disconnecting the electrical voltage. In this way, it is possible to achieve exact conveyance and measuring of a portion of fluid in the microchannels, as well as to prevent backflow and achieve precisely portioned and complete vaporisation. In this case, the effect of electrowetting is advantageously used.

Advantageously, an insulating layer comprising through-openings that extend through the insulating layer is provided between the flow-control layer and the substrate. It is thereby possible to effectively prevent undesired vaporisation of fluid in the fluid reservoir and/or in the flow-control layer and the flow holes therein during vaporisation. Undesired transfer of heat into the fluid reservoir is also prevented. In other words, the heat input into the substrate can be optimised and undesired heating or even vaporisation in portions that are upstream of the substrate and contain fluid can be reliably prevented.

Particularly advantageously, a voltage curve Uh(t) that is adjusted to the fluid mixture used is stored in a memory. The heater voltage characteristic Uh(t) is specified in a manner adjusted to the fluid mixture used, and the heating temperature of the substrate can be controlled temporally over the vaporisation process in accordance with the precisely known vaporisation kinematics of the relevant fluid mixture. In this way, it is possible to ensure optimal vaporisation of the fluid that is adjusted to the components thereof, and to reliably prevent the formation of undesired products of decomposition.

The heating temperature can be controlled or regulated at a high frequency, temporally over the vaporisation process.

According to a further aspect of the invention, a method for controlling an above-described vaporiser unit is provided. In this case, the heater voltage characteristic Uh(t) is advantageously specified in a manner adjusted to the fluid mixture used, and the heating temperature of the substrate is thus controlled temporally over the vaporisation process in accordance with the vaporisation kinematics of the relevant fluid mixture. In this way, it is possible to ensure optimal vaporisation of the fluid that is adjusted to the components thereof, and to reliably prevent the formation of undesired products of decomposition. Vaporisation that is configured in this manner makes it possible to optimise the heat input from the substrate into the fluid. Development of boundary layers between the fluid and the walls of the microchannels, in the form of vaporisation bubbles, which may prevent heat transfer or constitute a risk of local overheating, can be reliably reduced.

In the case of the operation known for known vaporising members, having a temperature that is set once and is constant throughout the vaporisation, the temperature is specified and set in a constant manner for vaporisation of the highest-boiling components in order to ensure complete vaporisation of the fluid, since it is assumed that lower-boiling components vaporise in any case when the maximum temperature is applied. The known operating principle conceals the risk that each lower-boiling component of the fluid consisting of a plurality of components may form vaporisation bubbles and thus a boundary layer between the fluid and the wall of the microchannels, and thus may prevent heat input. In a departure from this known manner of controlling the temperature in a vaporiser unit, the proposed method, in particular the further embodiments thereof, makes it possible to minimise boundary layer formation and achieve optimal heat input.

In this case, the duration of the individual vaporisation steps at different temperatures and/or vaporisation of the individual components of the individual portions of the fluid can be kept sufficiently short and/or can be carried out in a clocked manner at an actuation frequency such that the stepwise vaporisation is not perceptible for a consumer and it is nonetheless possible to ensure largely homogeneous, taste-compliant, repeatably precise aerosol formation. In particular, it is advantageous for a lower-boiling component of the fluid to initially be vaporised in a first vaporisation interval at a first temperature A, and for a higher-boiling component of the fluid to subsequently be vaporised in a second vaporisation interval at a second temperature B which exceeds the temperature A.

A portion of fluid that is conveyed into the vaporising member 60 is advantageously vaporised in a stepped manner at an actuation frequency for heating the substrate 63 in the range of from 1 Hz to 50 kHz, preferably in the range of from 30 Hz to 30 kHz, particularly preferably in the range of from 100 Hz to 25 kHz.

The invention will be explained in the following on the basis of preferred embodiments and with reference to the accompanying drawings, in which.

Figure 1:
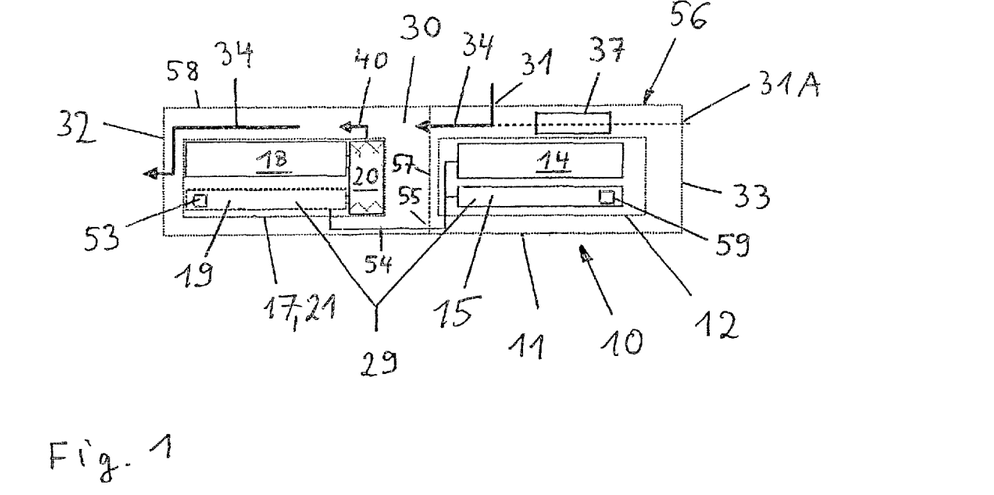
FIG. 1 is a cross-sectional view of an electronic cigarette product in an embodiment of the invention.

The electronic cigarette product 10 comprises a substantially rod-shaped or cylindrical housing 11. An air channel 30 is provided in the housing 11, between at least one air inlet opening 31 and the mouth end 32 of the cigarette product 10. In this case, the mouth end 32 of the cigarette product 10 refers to the end on which the consumer draws for the purpose of inhalation and thus applies a negative pressure to the cigarette product 10 and generates an air flow 34 in the air channel 30. At least one air inlet opening 31 may be arranged on the lateral face of the housing 11. In addition or alternatively, at least one air inlet opening 31A may be arranged at a remote end 33 of the cigarette product 10. The remote end 33 of the cigarette product 10 refers to the end of the cigarette product 10 that is opposite the mouth end 32.

An air heating means 37 for heating or preheating the incoming air can advantageously be arranged after one or both of the air inlets 31, 31A, in the flow path of the air flow 34. The aerosol formation can be optimised thereby. The air heating means 37 may for example be arranged adjacently to the energy supply unit 14 and/or extend in the peripheral direction around the inner lateral face of the housing 11.

Figure 3:
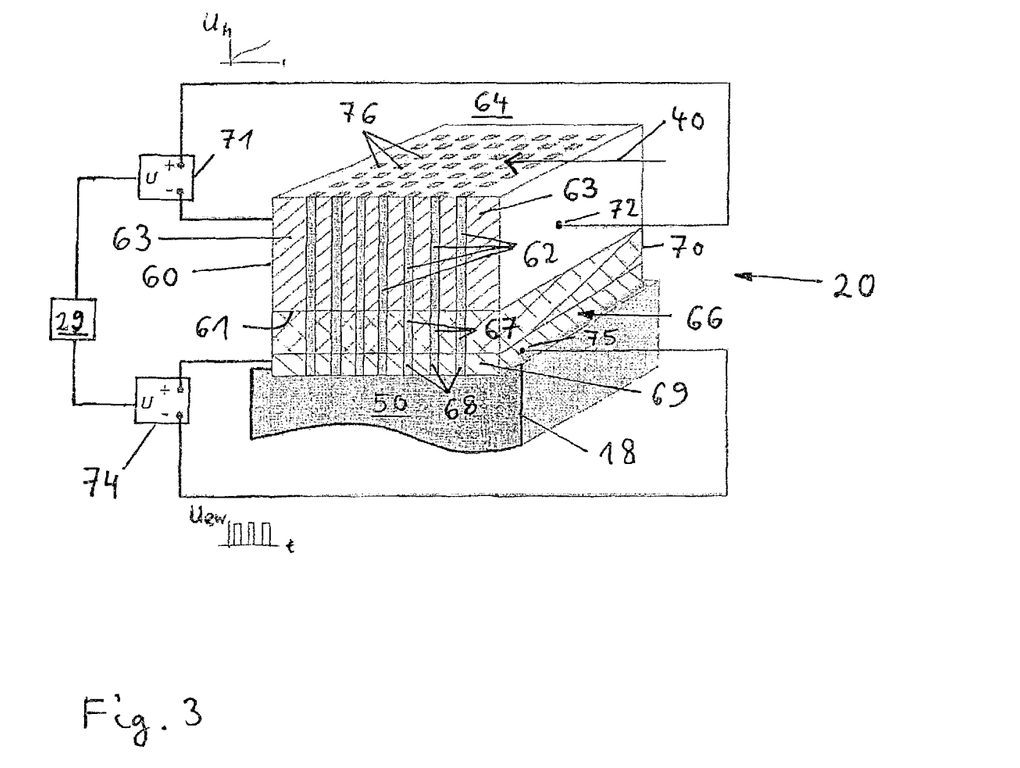
FIG. 3 is a perspective sectional view of a vaporiser unit.

The air sucked in through the inlet opening 31 is conveyed in the air channel 30, optionally via the interface or separation plane 57, to a vaporiser unit 20. The vaporiser unit 20 supplies fluid 50 from the fluid reservoir 18 into the airstream 34 as an addition 40, in the form of small drops of fluid as mist/aerosol, and/or in gaseous form as vapour. An advantageous volume of the fluid reservoir 18 is in the range between 0.1 ml and 5 ml, preferably between 0.5 ml and 3 ml, more preferably between 0.7 ml and 2 ml or 1.5 ml.

The cigarette product 10 comprises an electronic energy supply unit 12, advantageously at the remote end 33 of the cigarette product 10, which energy supply unit comprises an electrical energy store 14 and an electrical/electronic unit 15. The energy store 14 may in particular be an electrochemical primary cell or a rechargeable electrochemical battery, e.g. an Li-ion battery. The cigarette product 10 further comprises a consumable unit 17, advantageously at the mouth end 32 of the cigarette product 10, which consumable unit comprises a fluid reservoir 18, an electrical unit 19 and the vaporiser unit 20.

In place of the separate electrical/electronic units 15, 19, it is also possible to provide a common electrical/electronic unit, which may be arranged either in the energy supply unit 12 or in the consumable unit 17. The electrical/electronic units of the cigarette product 10 overall will be referred to in the following as a control assembly 29.

A sensor, for example a pressure sensor or a pressure or flow switch, is advantageously arranged in the housing 11, the control assembly being able, on the basis of a sensor signal emitted by the sensor, to identify an operating state of the cigarette product 10 in which a consumer draws on the mouth end 32 of the cigarette product 10 for the purpose of inhalation. In said operating state, the control assembly 29 actuates the vaporiser unit 20 so as to supply fluid 50 from the fluid reservoir 18 into the airstream 34 as an addition 40, in the form of small drops of fluid as mist/aerosol, and/or in gaseous form as vapour.

The fluid (i.e. the fluid component mixture) that is to be metered and is stored in the fluid reservoir 18 is for example a mixture of 1,2-propylene glycol, glycerol and/or water, into which one or more aromas (flavours) and/or active ingredients, such as nicotine, may be mixed.

The consumable unit 17 is advantageously designed as a cartridge 21 that can be replaced by the consumer, i.e. as a disposable part. The remainder of the cigarette product 10, which in particular contains the energy store 14, is advantageously designed as a base part 56 that can be reused by the consumer, i.e. as a reusable part. The cartridge 21 is designed such that it can be connected to the base part 56 and released from the base part 56 by the consumer. A separation plane or interface 57 is thus formed between the cartridge 21 and the reusable base part 56. The cartridge housing 58 may form part of the housing 11 of the cigarette product 10.

In other embodiments (see FIG. 2), the consumable unit 17 is designed as a cartridge 21 which the consumer can insert into and remove from the reusable base part 56 of the cigarette product 10. In this case, the cartridge housing 58 is a housing that is separate from the housing 11 of the cigarette product 10.

The cartridge 21 comprises at least the fluid reservoir 18. As shown in FIG. 2, the cartridge may comprise the electrical/electronic unit 19. In other embodiments, the electrical/electronic unit 19 is a completely or partially fixed component of the base part 56. Likewise, the vaporiser unit 20 may be part of the cartridge 21 or may be arranged in the base part 56. In some embodiments, the cartridge 21 may therefore substantially consist only of the fluid reservoir 18 and optionally the cartridge housing 58, it alternatively being possible for the cartridge housing 58 to be formed by the housing of the fluid reservoir 18, such that a separate cartridge housing 58 can be dispensed with.

In addition to being used in rod-shaped cigarette products 10, the cartridge 21 can also be used in other inhalers, for example in an electronic pipe, a shisha pipe, other heat-not-burn products, or a medical inhaler. The energy store 14 is generally not part of the cartridge 21, but instead part of the reusable base part 56.

The consumable unit 17 or the cartridge 21 advantageously comprises a non-volatile information memory 53 (see FIG. 1) for storing information or parameters relating to the consumable unit 17 or the cartridge 21, and is designed for example in the form of an EEPROM, RFID or another suitable form. The information memory 53 may be part of the electrical/electronic unit 19 or may be formed separately therefrom. The information memory 53 advantageously stores information relating to the ingredients, i.e. the composition, of the fluid stored in the fluid reservoir 18; information relating to the process profile, in particular the performance/temperature control; data relating to the state monitoring or system testing, for example leak testing; data relating to copy protection and protection against forgery, in particular comprising an ID for clear designation of the consumable unit 17 or cartridge 21; the serial number, manufacture date and/or expiry date; and/or the draw number (number of inhalation draws by the consumer) or the usage time. Advantageously, the memory 53 is or can be connected to the controller 15 of the base part 56 by means of contacts and/or wires.

FIG. 3 shows an advantageous embodiment of a vaporiser unit 20 according to the invention. The vaporiser unit 20 comprises a vaporising member 60 having a block-shaped substrate 63 consisting of an electrically conductive material, preferably silicon, doped ceramic, metal-ceramic, filter-ceramic, a semiconductor, in particular germanium, graphite, a metalloid and/or a metal. The substrate 63 is provided with a plurality of microchannels 62 which fluidically connect an inlet side 61 of the substrate 63 to an outlet side 64. The inlet side 61 is fluidically connected to the fluid reservoir 18. This will be explained in more detail in the following.

The average diameter of the microchannels 62 is preferably in the range between 5 μm and 100 μm, more preferably in the range between 10 μm and 50 μm, even more preferably in the range between 20 μm and 40 μm, and is for example 30 μm. Owing to these dimensions, a capillary effect is advantageously achieved, such that fluid penetrating into a microchannel 62 at the inlet side 61 rises upwards through the microchannel 62 until the microchannel 62 is filled with fluid.

The number of microchannels 62 is preferably in the range between four and 100. In this way, the heat input from the substrate into the microchannels 62 can be optimised and a guaranteed high vaporisation performance and a sufficiently large vapour discharge surface can be achieved.

The microchannels 62 are arranged in the form of a square, rectangular, polygonal, round, oval or differently shaped array, as can be seen in FIG. 3. The array may be designed in the form of a matrix having s columns and z rows, s advantageously being in the range between 2 and 50 and more advantageously in the range between 3 and 20, and/or z advantageously being in the range between 2 and 50, and more advantageously in the range between 3 and 20. In this way, it is possible to achieve an arrangement of the microchannels 62 that is effective and that can be produced in a simple manner, and that has guaranteed high vaporisation performance.

The cross section of the microchannels 62 may be square, rectangular, polygonal, round, oval or of a different shape, and/or may vary, in particular enlarge, reduce or remain constant, in portions in the longitudinal direction.

The length of one or each microchannel 62 is preferably in the range between 100 μm and 500 μm, more preferably in the range between 150 μm and 400 μm, even more preferably in the range between 180 μm and 370 μm, and is for example 300 μm. In this way, it is possible to achieve optimal fluid intake and portioning, while also having a sufficiently good heat input from the substrate 63 into the microchannels 62.

The spacing between two microchannels 62 is preferably at least 1.3 times the hydraulic diameter of one microchannel 62, the spacing being based on the centre axes of the two microchannels 62. The spacing may preferably be 1.5 to 5 times, more preferably 2 to 4 times, the hydraulic diameter of one microchannel 62. In this way, it is possible to achieve optimal heat input from the substrate into the microchannels, and a sufficiently stable arrangement and wall thickness of the microchannels.

The vaporiser unit 20 comprises a heater voltage source 71 which can preferably be controlled by the control unit 19 and which is connected to the substrate 63 by means of electrodes 72 at opposing sides thereof, such that an electrical voltage Uh generated by the heater voltage source 71 results in a current flow through the substrate 63. Owing to the ohmic resistance of the substrate 63, the current flow results in heating of the substrate 63 and thus in vaporisation of fluid contained in the microchannels 62. The vapour and/or aerosol generated in this way escapes from the microchannels 62 towards the outlet side 64 and is mixed into the air flow 34 as a vapour addition 40 (see FIG. 1). More precisely, when an airstream 34 through the air channel 30, resulting from the consumer drawing, is identified, the control assembly 29 actuates the heater voltage source 71, the fluid located in the microchannels 62 being forced out of the microchannels 62 in the form of vapour and/or aerosol 40, as a result of spontaneous heating. The generated vapour or the aerosol 40 is supplied to the optionally preheated air flow 34 in that said air flow flows past the outlet openings 76 of the vaporising member 60, on the outside thereof (see FIGS. 1 and 3).

Figure 2:
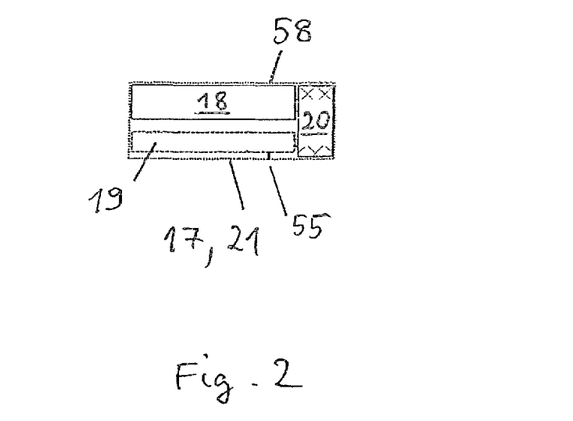
FIG. 2 is a cross-sectional view of a cartridge for an electronic cigarette product.

A voltage curve Uh(t) that is adjusted to the fluid mixture used is preferably stored in the memory 53 of the cartridge 21 or in a memory 59 of the base part 56. This makes it possible to specify the voltage curve Uh(t) in a manner adjusted to the liquid used, such that the heating temperature of the block or substrate 63, and thus also the temperature of the capillary microchannels 62, can be controlled temporally over the vaporisation process in accordance with the exactly known vaporisation kinematics of the relevant liquid, as a result of which optimal vaporisation results can be achieved. The vaporisation temperature is preferably in the range between 100° C. and 400° C., more preferably between 150° C. and 350° C., even more preferably between 190° C. and 290° C.

A flow controller 66 that controls the flow of fluid through the microchannels 62 is provided on the inlet side 61 of the substrate 60. In an advantageous embodiment, the flow controller 66 is a flow-control layer 69 comprising through-holes 68 that extend through the flow-control layer 69.

Particularly advantageously, an electric field can be applied to the fluid, in the flow-control layer 66, in order to influence the contact angle between the fluid and the inner wall of a through-hole 68, the effect of electrowetting preferably being used. For this purpose, the vaporiser unit 20 comprises an EW (electrowetting) voltage source 74 which can preferably be controlled by the control unit 19 and which is connected to the flow-control layer 69 by means of electrodes 75 at opposing sides thereof, such that an electrical voltage Uew generated by the EW voltage source 74 results in a displacement of the charge carriers in the fluid in the through-holes 68. In this way, it is possible to vary the contact angle between the fluid and the inner wall of a through-hole 68, between hydrophilic (a suitable voltage is applied) and hydrophobic (no voltage). If the contact angle in the through-holes 68 is set to hydrophilic, the fluid is conveyed out of the fluid reservoir 18 and into the through-holes 68 in a capillary manner, and can rise into the through-openings 67 and further into the microchannels 62 owing to the capillary conveying effect. If the contact angle in the through-holes 68 is set to hydrophobic, the fluid is prevented from rising out of the fluid reservoir 18, through the through-holes 68, into the through-openings 67 and into the microchannels 62. Since no capillary conveying effect arises, the fluid remains in the fluid reservoir 18. The function of the flow-control layer 69 is therefore that of allowing for switching between a free passage of fluid through the through-holes 68 and blocking a passage of fluid through the through-holes 68. The flow-control layer 69 can therefore also be referred to as a switching layer. According to the above, the flow-control layer 69 is used for controlling the filling process of the microchannels 62 in the vaporising member 60.

The flow-control layer 69 can advantageously or in addition be formed as an EWOD (electrowetting-on-dielectric) layer, the surface of the inner wall of the through-holes 68 being coated with a suitable dielectric. A dielectric of this kind can advantageously be formed as a self-assembled monolayer (SAM), by means of which the contact angle between the fluid and the inner wall of a through-hole 68 can be further or additionally influenced.

An insulating layer 70 consisting of an insulating material, for example glass or ceramic, and comprising through-openings 67 extending through the insulating layer 70 is advantageously provided between the flow-control layer 69 and the substrate 63. The insulating layer 70 is used to thermally insulate the vaporising member 60 from the fluid reservoir 18, in particular in order to prevent undesired significant heating and/or vapour formation of the fluid in the fluid reservoir 18 during the vaporisation. The insulating layer 70 may also be used for electrically insulating the substrate 63 from the flow-control layer 69, as a result of which the vaporisation and/or heating can be decoupled from the flow control. The through-openings 67 preferably correspond to the microchannels 62 and/or to the through-holes 68, such that continuous microchannels can be created from the fluid reservoir 18 to the outlet openings 76 on the outlet side 64 of the substrate 63.

The microchannels 62, through-openings 67 and/or through-holes 68 are preferably arranged such that the longitudinal axis thereof is transverse to the layers 69, 70. In general terms, when a layer sequence is formed by the substrate 63 and the flow-control layer 69 and/or the insulating layer 70 and/or at least one other layer, the microchannels 62 are arranged such that the longitudinal axes thereof are advantageously transverse to the layer sequence. In this way, it is possible to achieve optimal heat input from the substrate 63 into the microchannels 62 and to keep the microchannels 62 largely free of sealing problems. Furthermore, a plurality or all of the layers of the layer sequence are advantageously of different or the same layer thicknesses, and specifically, preferably in particular a layer thickness of less than or equal to 500 μm in each case. In this way, it is possible to achieve optimal heat input from the substrate 63 into the microchannels 62 and to keep the microchannels 62 largely free of sealing problems. In this case, the vaporising member 60 may advantageously be produced from segments of a wafer by means of thin-film layer technology, which wafer is of a conventional layer thickness.

The microchannels 62, through-openings 67 and/or through-holes 68 may have passage cross sections that are the same or that are different from one another. The number K1 of microchannels 62, the number K2 of through-openings 67 and/or the number K3 of through-holes 68 may differ from one another. In particular, K1 may be greater than K2 and/or greater than K3. K2 may be greater than K3. A group of microchannels 62, in particular having a group number G1 that is less than or equal to K1, may be associated with a single through-opening 67 and/or a single through-hole 68, the cross section of which is adjusted to, in particular corresponds to or exceeds, the cross section of the group of microchannels 62. In this way, a group of a plurality of microchannels 62 having a smaller number of through-openings 67 can be selectively blocked and/or released, and simpler manufacture can be achieved. In this way, it is possible to achieve a group of a plurality of microchannels 62 having a smaller number of through-holes 68 for supplying with fluid, and to achieve simpler manufacture. In a manner deviating from the embodiment shown in FIG. 3, it is possible for example for a group having a group number G1 of from 3 to 10 microchannels 62 to be associated with a common through-opening 67 and/or a common through-hole 68. In this case, the through-opening 67 and/or the through-hole 68 extends over the 3 to 10 microchannels 62.

Instead of using the electrowetting effect, it is also possible for other flow-controlling elements to be provided in the flow-control layer 69 or more generally in the flow controller 66, for example one or more throttles and/or one or more controllable (micro)valves. If the capillary action of the microchannels 62, through-openings 67 and/or through-holes 68 is not sufficient for conveying a sufficient amount of fluid from the fluid reservoir 18 into the vaporising member 60, additional or alternative conveying mechanisms may be provided, for example by means of pressure application, one or more (micro)pumps, or the like.

The vaporiser unit 29 is set such that an advantageous amount of fluid in the range between 1 μl and 20 μl, more preferably between 2 μl and 10 μl, even more preferably between 3 μl and 5 μl, typically 4 μl per draw by the consumer is metered. The vaporiser unit 29 may preferably be adjustable with respect to the amount of fluid per draw.

The metering device/vaporiser combination can advantageously be set such that primarily fluid droplets having a diameter in the range between 0.05 μm and 5 μm, preferably between 0.1 μm and 3 μm, result. Droplet sizes in the range between 0.05 and 5 MMAD (mass median aerodynamic diameter), preferably between 0.1 and 3 MMAD, more preferably between 0.5 and 2 MMAD, even more preferably between 0.7 and 1.5 MMAD, for example approximately 1 MMAD, may be optimal. MMAD corresponds to an EU standard and is specified in μm.

The fact that the voltage source 74 of the flow controller 66 and the voltage source 71 of the vaporising member 60 are separately electrically connected to the control assembly 29 and are actuated separately from one another means that an advantageous functional separation between the conveying/metering and the vaporisation is achieved.

The progression of the vaporisation process will be explained in the following with reference to FIG. 4A to 4E.

In the initial state shown in FIG. 4A, the voltage source 74 for the filling process is de-energised, and the contact angle between the fluid and the inner wall of the through-holes 68 is hydrophobic, such that no fluid can reach through the through-holes 68.

FIG. 4B shows the filling process. The voltage source 74 for the filling process is activated, and the contact angle between the fluid and the inner wall of the through-holes 68 becomes hydrophilic, such that fluid flows, by means of a capillary effect, through the through-holes 68 and the through-openings and into the microchannels 62 of the vaporiser 60.

The filling process is completed (FIG. 4C) when all the microchannels 62 are filled as far as the outlet side 64 of the vaporiser 60. In the filled state, the conveying effect ceases because, when the outlet side 64 is reached, a capillary conveying force is no longer applied. The microchannels 62 can also be filled only in part, by means of purposeful actuation of the flow-control layer 69.

The amount to be vaporised in each case can thus be specified by means of the geometry, in particular the length, of the microchannels 62 or the thickness of the substrate 63, and/or by actuating the flow-control layer 69. In general, the length of the microchannels 62 is large in relation to the average diameter thereof, in particular larger by at least a factor of three, for example by a factor in the range between 3 and 30, preferably between 5 and 20, for example by a factor of 10. As a result, the invention can be delimited from known lattices or grids (known as meshes).

It is conceivable to use or actuate vaporising members 60 having substrates 63 of different thicknesses, in one or different inhalers, in order to generate more or less vapour per vaporisation process/draw.

Following the filling process, the voltage source 71 for the vaporising member 60 is activated (heating process, FIG. 4D). In this case, the voltage Uh is guided such that the vaporising temperature over the substrate 63, i.e. in the microchannels 62, can be set so as to be adjusted to the individual vaporisation behaviour of the fluid mixture used. This prevents the risk of local overheating, and thus the formation of harmful substances, also owing to the large surface of the channel inner wall relative to the liquid.

EMBODIMENTS

Embodiment 1. Vaporiser unit (20) for an inhaler, comprising a vaporising member (60) that comprises an inlet side (61), an outlet side (64), a plurality of microchannels (62), a substrate (63), and a resistance heating element (65) for vaporising fluid conveyed through the microchannels (62), characterised in that

- the microchannels (62) each extend through the substrate (63), from the inlet side (61) to the outlet side (64),
- the substrate (63) is electrically conductive, and
- the resistance heating element (65) is formed by the substrate (63).

Embodiment 2. Vaporiser unit according to embodiment 1, characterised in that the microchannels (62) are each surrounded by the substrate (63) in the peripheral direction.

Embodiment 3. Vaporiser unit according to either of the preceding embodiments, characterised in that a flow controller (66) that controls the flow of fluid through the microchannels (62) is provided on the inlet side (61) of the substrate (63).

Embodiment 4. Vaporiser unit according to embodiment 3, characterised in that the flow controller (66) is a flow-control layer (69) comprising through-holes (68) that extend through the flow-control layer (69).

Embodiment 5. Vaporiser unit according to embodiment 4, characterised in that the contact angle between the fluid and the inner wall of one or each through-hole (68) can be varied by means of applying an electrical voltage that can be generated by a voltage source.

Embodiment 6. Vaporiser unit according to either embodiment 4 or embodiment 5, characterised in that an insulating layer (70) comprising through-openings (67) that extend through the insulating layer (70) is provided between the flow-control layer (69) and the substrate (63).

Embodiment 7. Vaporiser unit according to any of the preceding embodiments, characterised in that the average diameter of one or each microchannel (62) is in the range between 5 µm and 100 µm, preferably between 10 µm and 50 µm, more preferably between 20 µm and 40 µm.

Embodiment 8. Vaporiser unit according to any of the preceding embodiments, characterised in that the number of microchannels (62) is in the range between 4 and 100.

Embodiment 9. Vaporiser unit according to any of the preceding embodiments, characterised in that the microchannels (62) are arranged in the form of an array, in particular in the form of columns and rows.

Embodiment 10. Vaporiser unit according to embodiment 9, characterised in that the number s of columns is in the range between 2 and 50, preferably between 3 and 20, and/or the number z of rows is in the range between 2 and 50, preferably between 3 and 20.

Embodiment 11. Vaporiser unit according to any of the preceding embodiments, characterised in that the length of one or each microchannel (62) is in the range between 100 µm and 500 µm, preferably between 150 µm and 400 µm, particularly preferably between 180 µm and 370 µm.

Embodiment 12. Vaporiser unit according to any of the preceding embodiments, characterised in that the length of one or each microchannel (62) corresponds to the thickness of the substrate (63).

Embodiment 13. Vaporiser unit according to any of the preceding embodiments, characterised in that the spacing between mutually adjacent microchannels (62), based on the centre axes of mutually adjacent microchannels (62), is in the range between 1.3 times and 5 times, preferably between 1.5 times and 4.5 times, particularly preferably in the range between twice and 4 times, the diameter of one microchannel (62).

Embodiment 14. Vaporiser unit according to any of the preceding embodiments, characterised in that a layer sequence is formed by the substrate (63) and the flow-control layer (69) and/or the insulating layer (70) and/or at least one other layer.

Embodiment 15. Vaporiser unit according to embodiment 14, characterised in that the microchannels (62) are arranged such that the longitudinal axes thereof are transverse to the layer sequence.

Embodiment 16. Vaporiser unit according to either embodiment 14 or embodiment 15, characterised in that a plurality or all of the layers of the layer sequence are of different or the same layer thicknesses, preferably in particular a layer thickness of less than or equal to 500 µm in each case.

Embodiment 17. Vaporiser unit according to any of the preceding embodiments comprising a memory (53; 59), characterised in that a voltage curve Uh(t) that is adjusted to the fluid mixture used is stored in the memory (53; 59) of the vaporiser unit (20).

Embodiment 18. Vaporiser unit according to any of the preceding embodiments, characterised in that the vaporiser unit (20) is a common micro-electro-mechanical system.

Embodiment 19. Vaporiser unit according to any of the preceding embodiments, characterised in that the number K1 of microchannels (62), the number K2 of through-openings (67) and/or the number K3 of through-holes (68) differ from one another, and/or a group of microchannels (62), in particular having a group number G1 that is less than or equal to K1, is associated with a single through-opening (67) and/or a single through-hole (68).

Embodiment 20. Inhaler (10) comprising a vaporiser unit (20) according to any of the preceding embodiments.

Embodiment 21. Method for controlling a vaporiser unit (20) according to any of embodiments 1 to 19.

Embodiment 22. Method according to embodiment 21, characterised in that the heater voltage characteristic Uh(t) is specified in a manner adjusted to the fluid mixture used, and the heating temperature of the substrate (63) is thus controlled temporally over the vaporisation process in accordance with the vaporisation kinematics of the relevant fluid mixture.

Embodiment 23. Method according to either embodiment 21 or embodiment 22, characterised in that a portion of fluid is conveyed into the vaporising member (60), the microchannels (62) are filled with fluid, in accordance with the number thereof and over the length thereof that extends from the inlet side (61) to the outlet side (64), by means of sub-portions of the portion of fluid, and are largely closed on the inlet side (61), and the portion of fluid is vaporised by means of a voltage being applied to the substrate (63), the vapour emerging on the outlet side (64) and in particular the vaporisation occurring in a stepped manner over time and having a differently set temperature.

Embodiment 24. Method according to embodiment 23, characterised in that initially a lower-boiling component of the fluid is vaporised in a first vaporisation interval at a first temperature A, and subsequently a higher-boiling component of the fluid is vaporised in a second vaporisation interval at a second temperature B which exceeds the temperature A.

Embodiment 25. Method according to any of embodiments 21 to 24, characterised in that the vaporisation of a portion of fluid that is conveyed into the vaporising member (60) occurs in a stepped manner at an actuation frequency for heating the substrate (63) in the range of from 1 Hz to 50 kHz, preferably in the range of from 30 Hz to 30 kHz, particularly preferably in the range of from 100 Hz to 25 kHz.

As soon as all the fluid has vaporised, the heater voltage source 71 is deactivated. Since the liquid properties and amount are advantageously known exactly, this timepoint can be controlled very accurately. The energy intake of a vaporiser unit 20 of this kind can therefore be reduced compared with known methods, since the vaporising energy required can be introduced in a far more metered, and thus more exact, manner.

Since the flow-control layer 69 is deactivated during the vaporisation process, there is no feedback effect with the remainder of the liquid in the fluid reservoir 18, i.e. no concentration change occurs in the fluid reservoir 18. The vaporisation or active agent metering is therefore largely identical over all draws, because the liquid that is vaporised is always of the same composition.

Figures 4A, 4B, 4C, 4D, 4E:
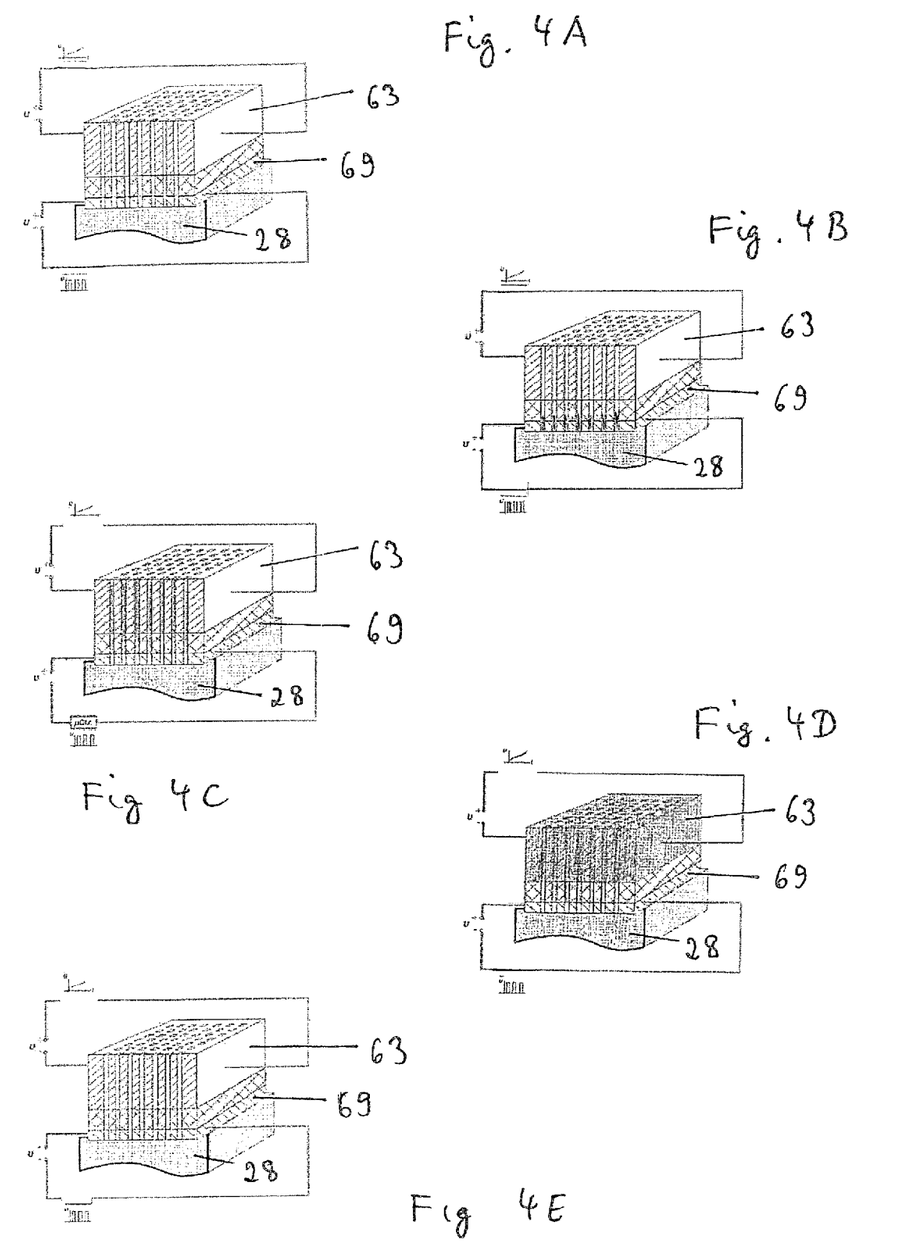
FIG. 4A-4E show the vaporiser unit according to FIG. 3 in different states of the vaporisation process.

After the heating process has been completed (FIG. 4E), the microchannels 62 are emptied. A liquid residue which may remain in the through-openings 67 of the insulating layer 70 can be reduced structurally by means of the thickness ratio among the layers 63, 69, 70, or is negligible compared with the amount of liquid vaporised per draw. It is thus possible to begin again with the next vaporisation process, in FIG. 4A, using a defined, constant liquid composition.

The voltage sources 71, 74 are advantageously electrically actuated at a suitable actuation frequency that is typically in the Hz or kHz range and is for example between 1 Hz and 50 kHz, preferably between 30 Hz and 30 kHz, particularly preferably between 100 Hz and 25 kHz. In an alternative embodiment, the actuation frequency for the voltage source 74 may be in the range between 5 Hz and 50 Hz, preferably between 10 Hz and 40 Hz.

The vaporiser unit 20 is preferably produced on the basis of MEMS technology and is therefore advantageously a micro-electro-mechanical system.

The invention claimed is:

1. A vaporiser unit for an inhaler, comprising:
a vaporising member,
wherein the vaporising member comprises:
   an inlet side;
   an outlet side;
   a plurality of microchannels;
   a substrate; and
   a resistance heating element for vaporising fluid conveyed through the microchannels of the plurality of microchannels,
wherein the microchannels of the plurality of microchannels each extend through the substrate, from the inlet side to the outlet side,
wherein the substrate is electrically conductive,
wherein the resistance heating element is formed by the substrate,
wherein a flow controller that controls the flow of fluid through the microchannels of the plurality of microchannels is provided on an inlet side of the substrate, and
wherein the flow controller is a flow-control layer comprising through-holes that extend through the flow-control layer.

2. The vaporiser unit according to claim 1,
wherein the microchannels of the plurality of microchannels are each surrounded by the substrate in a peripheral direction.

3. The vaporiser unit according to claim 1,
wherein a contact angle between the fluid and an inner wall of one or each through-hole can be varied by applying an electrical voltage generated by a voltage source.

4. The vaporiser unit according to claim 1,
wherein an insulating layer comprising through-openings that extend through the insulating layer is provided between the flow-control layer and the substrate.

5. The vaporiser unit according to claim 1,
wherein an average diameter of one or each microchannel of the plurality of microchannels is in a range between 5 μm and 100 μm.

6. The vaporiser unit according to claim 1,
wherein a number of microchannels of the plurality of microchannels is in a range between 4 and 100.

7. The vaporiser unit according to claim 1,
wherein the microchannels of the plurality of microchannels are arranged in a form of an array.

8. The vaporiser unit according to claim 7,
wherein a number s of columns of the array is in a range between 2 and 50, and/or a number z of rows of the array is in a range between 2 and 50.

9. The vaporiser unit according to claim 1,
wherein a length of one or each microchannel of the plurality of microchannels is in a range between 100 μm and 500 μm.

10. The vaporiser unit according to claim 1,
wherein a length of one or each microchannel of the plurality of microchannels corresponds to a thickness of the substrate.

11. The vaporiser unit according to claim 1,
wherein a spacing between mutually adjacent microchannels of the plurality of microchannels, based on centre axes of the mutually adjacent microchannels of the plurality of microchannels, is in a range between 1.3 times and 5 times a diameter of one microchannel of the plurality of microchannels.

12. The vaporiser unit according to claim 4,
wherein a layer sequence is formed by the substrate, the flow-control layer, the insulating layer, and/or at least one other layer.

13. The vaporiser unit according to claim 12,
wherein the microchannels of the plurality of microchannels are arranged such that longitudinal axes thereof are transverse to the layer sequence.

14. The vaporiser unit according to claim 12,
wherein a plurality or all layers of the layer sequence are of different or the same layer thicknesses, each layer having a layer thickness of less than or equal to 500 μm in each case.

15. The vaporiser unit according to claim 1, further comprising:
a memory,
wherein a heater voltage curve Uh(t) applied to the resistance heating element, which is adjusted to a fluid mixture used, is stored in the memory.

16. The vaporiser unit according to claim 1,
wherein the vaporiser unit is a common micro-electro-mechanical system.

17. An inhaler, comprising:
a vaporiser unit according to claim 1.

18. A method for controlling a vaporiser unit, comprising:
providing a vaporiser unit according to claim 1; and
controlling the vaporiser unit via:
   controlling a heater voltage curve Uh(t) applied to the resistance heating element; and/or
   controlling a flow of fluid through the microchannels of the plurality of microchannels.

19. The method according to claim 18,
wherein the heater voltage curve Uh(t) applied to the resistance heating element is specified in a manner adjusted to a fluid mixture used, and a heating temperature of the substrate is thus controlled temporally over a vaporisation process in accordance with a vaporisation kinematics of a relevant fluid mixture.

20. The method according to claim 18,
wherein a portion of fluid is conveyed into the vaporising member, the microchannels of the plurality of microchannels are filled with fluid, in accordance with a number thereof and over a length thereof that extends from the inlet side to the outlet side, by sub-portions of the portion of fluid, and are largely closed on the inlet side, and the portion of fluid is vaporised by the heater voltage curve Uh(t) being applied to the resistance heating element, the vapour emerging on the outlet side and the vaporisation occurring in a stepped manner over time and having a differently set temperature.

21. The method according to claim 20,
wherein initially a lower-boiling component of the fluid is vaporised in a first vaporisation interval at a first temperature A, and subsequently a higher-boiling component of the fluid is vaporised in a second vaporisation interval at a second temperature B which exceeds the temperature A.

22. The method according to claim 18,
wherein vaporisation of a portion of fluid that is conveyed into the vaporising member occurs in a stepped manner at an actuation frequency for the heater voltage curve Uh(t) applied to the resistance heating element in a range of from 1 Hz to 50 kHz.

23. A method for controlling a vaporiser unit, comprising:
providing a vaporiser unit, wherein the vaporiser unit comprises:
  a vaporising member,
  wherein the vaporising member comprises:
    an inlet side;
    an outlet side;
    a plurality of microchannels;
    a substrate; and
    a resistance heating element for vaporising fluid conveyed through the microchannels of the plurality of microchannels,
  wherein the microchannels of the plurality of microchannels each extend through the substrate, from the inlet side to the outlet side,
  wherein the substrate is electrically conductive, and
  wherein the resistance heating element is formed by the substrate; and
controlling the vaporiser unit via:
  controlling a heater voltage curve Uh(t) applied to the resistance heating element; and/or
  controlling a flow of fluid through the microchannels of the plurality of microchannels,
wherein a portion of fluid is conveyed into the vaporising member, the microchannels of the plurality of microchannels are filled with fluid, in accordance with a number thereof and over a length thereof that extends from the inlet side to the outlet side, by sub-portions of the portion of fluid, and are largely closed on the inlet side, and the portion of fluid is vaporised by the heater voltage curve Uh(t) being applied to the resistance heating element, the vapour emerging on the outlet side and the vaporisation occurring in a stepped manner over time and having a differently set temperature, and
wherein initially a lower-boiling component of the fluid is vaporised in a first vaporisation interval at a first temperature A, and subsequently a higher-boiling component of the fluid is vaporised in a second vaporisation interval at a second temperature B which exceeds the temperature A.

* * * * *